(12) United States Patent
Buchanan et al.

(10) Patent No.: US 11,664,122 B2
(45) Date of Patent: May 30, 2023

(54) PATIENT SUPPORT APPARATUS TRACKING SYSTEM

(71) Applicant: Hill-Rom Services, Inc., Batesville, IN (US)

(72) Inventors: Neil Buchanan, Greensburg, IN (US); Michael R. Montini, Batesville, IN (US); Gregory John Shannon, Indianapolis, IN (US); Brandon Fisk, Brookville, IN (US); Rachel L. Williamson, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 265 days.

(21) Appl. No.: 16/904,644

(22) Filed: Jun. 18, 2020

(65) Prior Publication Data

US 2020/0402654 A1    Dec. 24, 2020

Related U.S. Application Data

(60) Provisional application No. 62/863,515, filed on Jun. 19, 2019.

(51) Int. Cl.
*G16H 40/40*    (2018.01)
*G16H 40/67*    (2018.01)
(Continued)

(52) U.S. Cl.
CPC .............. *G16H 40/40* (2018.01); *A61G 7/05* (2013.01); *G16H 40/20* (2018.01); *G16H 40/67* (2018.01);
(Continued)

(58) Field of Classification Search
CPC ........ G16H 40/40; G16H 40/20; G16H 40/67; A61G 7/05; A61G 2203/20; A61G 2205/60
See application file for complete search history.

(56) References Cited

U.S. PATENT DOCUMENTS 8,461,968 B2    6/2013  Ball et al.
2007/0013516 A1 *  1/2007  Freitag ............... H04L 65/1101
                                                340/572.1

(Continued)

FOREIGN PATENT DOCUMENTS

CN    101630387 A       1/2010
EP       1820524 A1 *   8/2007   ........ A61M 5/14546
EP       3189823 A1     7/2017

*Primary Examiner* — Nabil H Syed
*Assistant Examiner* — Cal J Eustaquio
(74) *Attorney, Agent, or Firm* — Price Heneveld LLP

(57) ABSTRACT

A patient support apparatus tracking system includes at least one of a frame, mattress, and mattress cover. A radio-frequency identification (RFID) tag may be embedded within the at least one of the frame, mattress, and mattress cover. The RFID tag may include an identification memory unit including read-only sort-prefix data corresponding to the one of the frame, mattress, and mattress cover and a service memory unit comprising a read/write configuration including a greater amount of digital storage than the identification memory unit. The RFID tag may be configured to receive a log of configurable equipment updates into the service memory unit and communicate the sort-prefix from the identification memory unit and the log of equipment updates to a controller via a reader device.

18 Claims, 4 Drawing Sheets

(51) Int. Cl.
*G16H 40/20* (2018.01)
*A61G 7/05* (2006.01)

(52) U.S. Cl.
CPC ...... *A61G 2203/20* (2013.01); *A61G 2205/60* (2013.01)

(56) References Cited

U.S. PATENT DOCUMENTS

| | | | |
|---|---|---|---|
| 2007/0273517 A1* | 11/2007 | Govind | G16H 10/60 340/572.1 |
| 2009/0153321 A1* | 6/2009 | Lange | G01V 15/00 340/539.1 |
| 2012/0280046 A1* | 11/2012 | Muirhead | H01Q 21/24 235/492 |
| 2013/0239330 A1 | 9/2013 | Newlin | |
| 2015/0205985 A1 | 7/2015 | Jinadatha | |
| 2016/0259906 A1* | 9/2016 | Iucha | A61G 7/00 |
| 2017/0181909 A1* | 6/2017 | Baker, Jr. | A61G 7/0522 |
| 2017/0196743 A1 | 7/2017 | Wiggermann et al. | |
| 2018/0228678 A1* | 8/2018 | Sauser | A61G 7/05776 |
| 2019/0132008 A1* | 5/2019 | Jang | H03M 13/03 |
| 2020/0002872 A1* | 1/2020 | Kim | G05B 15/02 |

\* cited by examiner

PATIENT SUPPORT APPARATUS TRACKING SYSTEM

CROSS-REFERENCE TO RELATED APPLICATION

This application claims priority to and the benefit under 35 U.S.C. § 119(e) of U.S. Provisional Application No. 62/863,515, filed on Jun. 19, 2019, entitled "PATIENT SUPPORT APPARATUS TRACKING SYSTEM," the disclosure of which is hereby incorporated herein by reference in its entirety.

FIELD OF THE DISCLOSURE

The present disclosure generally relates to a patient support apparatus tracking system, and more specifically to patient support apparatus tracking system with radio-frequency identification tags.

SUMMARY OF THE DISCLOSURE

According to one aspect of the present disclosure, a patient support apparatus tracking system includes a first mattress cover including a first radio-frequency identification (RFID) tag. The first RFID tag includes a first identification memory unit including first identity data for the first mattress cover. The first identity data includes a sort-prefix and a serial number. The first RFID tag also includes a first service memory unit including first service data corresponding to services performed on the first mattress cover. A second mattress cover includes a second RFID tag. The second RFID tag includes a second identification memory unit including second identity data for the second mattress cover. The second identity data includes a sort-prefix and a serial number different from the first identity data in the first RFID tag. The second RFID tag also includes a second service memory unit including second service data corresponding to services performed on the second mattress cover. A controller is configured to cingulate each of the first and second RFID tags using the sort-prefix from the first and second identification memory units, write an equipment update into the first and second service memory units and communicate an equipment status of each of the first and second mattress covers based on the first and second identity data for the first and second mattress covers to one of a display and remote device.

According to another aspect of the present disclosure, a patient support apparatus tracking system includes at least one of a frame, mattress, and mattress cover. A radio-frequency identification (RFID) tag is embedded within the at least one of the frame, mattress, and mattress cover. The RFID tag includes an identification memory unit including read-only sort-prefix data corresponding to the one of the frame, mattress, and mattress cover and a service memory unit having a read/write configuration including a greater amount of digital storage than the identification memory unit. The RFID tag is configured to receive a log of configurable equipment updates into the service memory unit and communicate the sort-prefix from the identification memory unit and the log of equipment updates to a controller via a reader device.

According to yet another aspect of the present disclosure, a patient support apparatus tracking system includes a first mattress cover including a first radio-frequency identification (RFID) tag. The first RFID tag includes a first identification memory unit including first fixed data corresponding to the identity of the first mattress cover and a first service memory unit including first configurable data corresponding to services performed on the first mattress cover. A second mattress cover includes a second RFID tag. The second RFID tag includes a second identification memory unit including second fixed data corresponding to the identity of the second mattress cover. The second fixed data in the second RFID tag is different from the first fixed data in the first RFID tag. A second service memory unit includes second configurable data corresponding to services performed on the second mattress cover. The first and second RFID tags are configured to communicate the first and second fixed data and the first and second configurable data via a controller. The first and second configurable data is processed based on the identity of the first and second mattress covers.

These and other features, advantages, and objects of the present invention will be further understood and appreciated by those skilled in the art by reference to the following specification, claims, and appended drawings.

DETAILED DESCRIPTION

Figure 1:
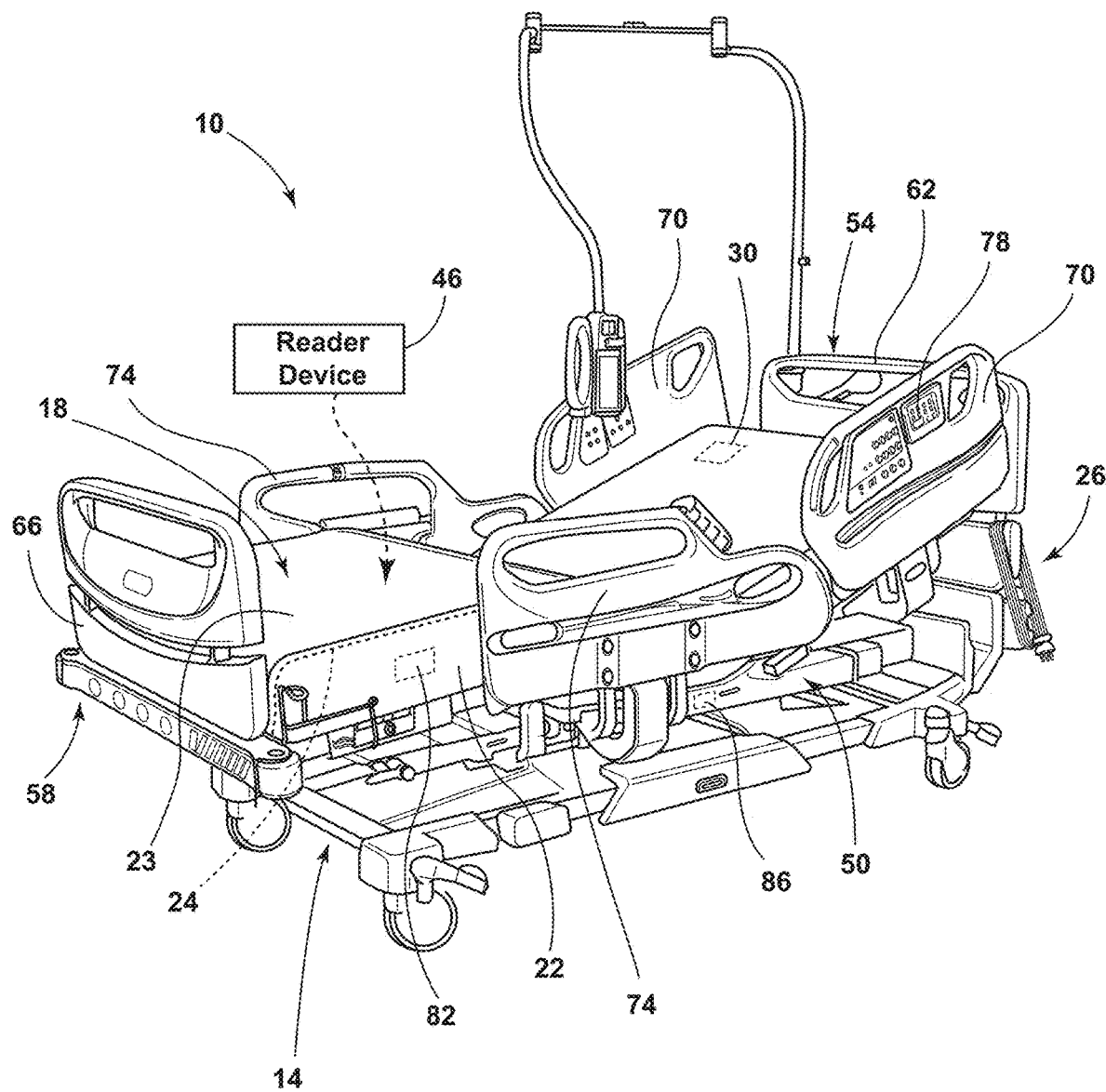
FIG. 1 is a is a perspective view of a patient support apparatus, according to various aspects described herein.

The present illustrated embodiments reside primarily in combinations of method steps and apparatus components related to a patient support apparatus tracking system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Figure 2:
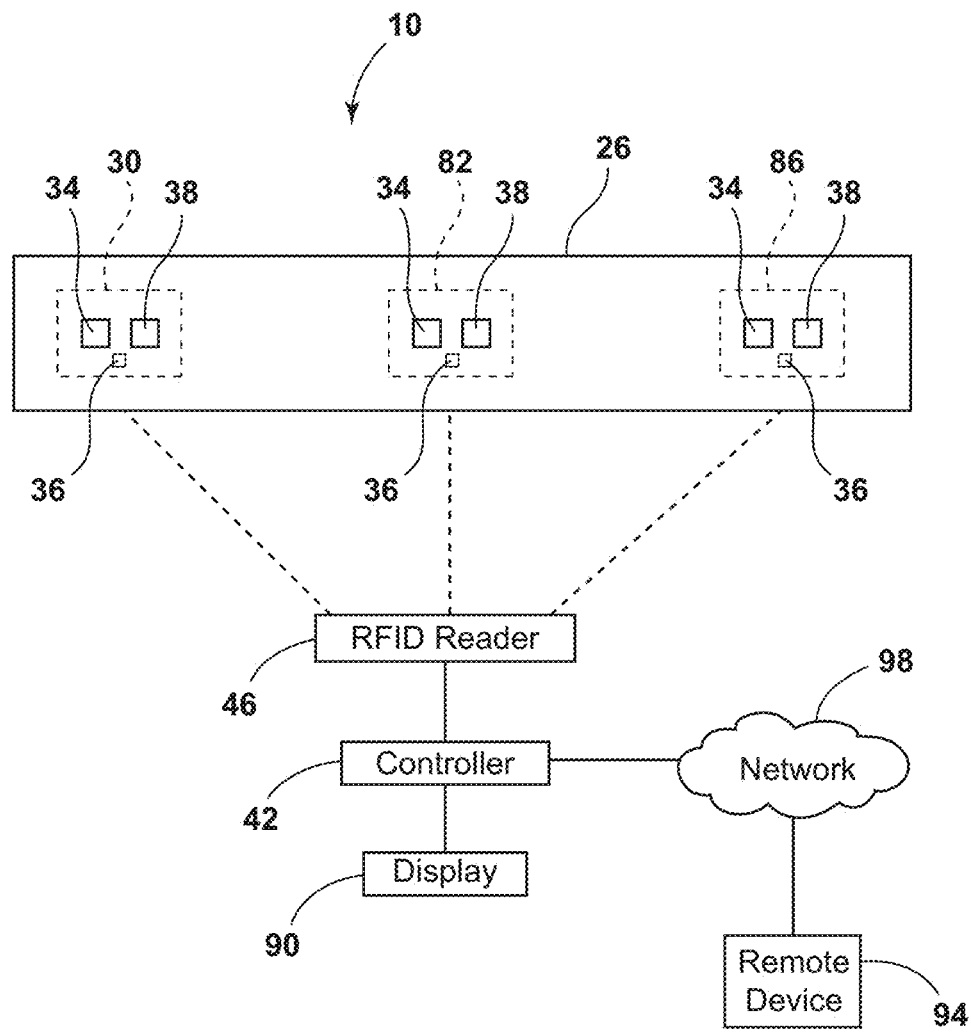
FIG. 2 is a diagram of a patient support apparatus tracking system for the patient support apparatus of FIG. 1 according to various aspects described herein.

Referring to FIGS. 1-2 reference numeral 10 generally designates a patient support apparatus tracking system including at least one of a frame 14, a mattress 18, and a mattress cover 22. The frame 14, mattress 18, and mattress cover 22 may be components of a patient support apparatus 26, which may be in the form of a bed. A radio-frequency identification (RFID) tag 30 is embedded within the at least one of the frame 14, mattress 18, and mattress cover 22. The RFID tag 30 includes a first memory unit 34 comprising a sort-prefix and a second memory unit 38. The RFID tag 30 is configured to receive an equipment update into the second memory unit 38. Furthermore, the patient support apparatus tracking system 10 is configured to cingulate the RFID tag 30 by communicating the sort-prefix from the first memory unit 34 to a controller 42 via a reader device 46.

Referring now to FIG. 1, the patient support apparatus 26 may include a hospital bed. While described as the patient support apparatus 26, it is within the scope of the disclosure that the patient support apparatus 26 may include a bed frame, a mattress, or any suitable structure for supporting a patient, including, but not limited to: other types of beds, surgical tables, examination tables, stretchers, and the like.

In some examples, the frame 14 may be in the form of a base frame 14, and an upper frame 50 may be coupled with the base frame 14. The upper frame 50 may be operable between raised, lowered, and tilted positions relative to the base frame 14. The patient support apparatus 26 may include a surface, which may be formed by the mattress 18, supported by one of the base frame 14 and the upper frame 50. The mattress 18 may be in the form of a cushion including a foam base and multiple layers, but is not limited to such a configuration. For example, the mattress 18 may not include a foam base. In some examples, bladders, springs, beads, gel and the like may be included in the mattress 18. The bladders may be in the form of air or foam. Additionally, the mattress 18 may include componentry such as air compressors, hoses, electronic components and valves, material fire barriers etc.

The mattress 18 may be encased in the mattress cover 22, which may be removable from the mattress 18 for washing and/or replacing the mattress cover 22. In some aspects, the mattress 18 includes more than one mattress cover 22, which may include a first, or top, cover 23 and a second, or bottom, cover 24. The bottom cover 24 may be positioned underneath the top mattress cover 23 such that the bottom mattress cover 24 is disposed between the top mattress cover 24 and the mattress 18. In some examples, the bottom mattress cover 24 is made of a different material than the top mattress cover 23. For example, the bottom mattress cover 24 may include a waterproof or water resistant material (i.e. a vinyl material), while the top mattress cover 24 includes a breathable material (i.e. a cotton material). The patient support apparatus 26 may also include sheets for covering the mattress 18 and/or the mattress cover 22.

The patient support apparatus 26 may include a head end 54 and a foot end 58. A headboard 62 may be provided at the head end 54 and a footboard 66 may be provided at the foot end 58. The patient support apparatus 26 may include a pair of head siderail assemblies 70 and a pair of foot siderail assemblies 74. In some examples, a graphical user interface 78 may be coupled to an external side of at least one siderail of the head and foot siderail assemblies 70, 74.

As illustrated in FIG. 1, the patient support apparatus tracking system 10 may include multiple RFID tags 30. The RFID tag 30 may be embedded into the mattress 18. RFID tags 82 may be embedded into the mattress cover(s) 22, 23, and 24. Yet another RFID tag 86 may be embedded into the frame 14. However, in some examples, the RFID tag 30 may be coupled with any component of the patient support apparatus 26. For example, the RFID tag 30 may be coupled with the head, foot, and/or side rail assemblies 70, 74 or a sheet covering the mattress 18. Additionally, the RFID tags 30, 82, 86 may be utilized alone, or in combination with each other.

With reference to FIG. 2, the controller 42 may be in communication with the reader device 46 for gathering input from the RFID tags 30, 82, 86, processing the input, and generating an output in response to the input. In some examples, the controller 42 may be in the form of a microcontroller and may include one or more central processing units (CPUs), or microprocessors, a memory, and/or programmable input/output ports. The input may be provided to the controller 42 from the multiple RFID tags 30, 82, 86. Thus, the reader device 46 may be in the form of a RFID reader configured to send a signal to at least one of the multiple RFID tags 30, 82, 86 and read the response. In some examples, the reader device 46 is a passive reader which only receives signals from the multiple RFID tags 30, 82, 86. In further examples, the reader device 46 is an active reader which transmits interrogator signals and receives replies from at least one of the multiple RFID tags 30, 82, 86. The controller 42 may read, convert, or analyze, the input and determine data to write into to the multiple RFID tags 30, 82, 86.

The reader device 46 may be in the form of a portable or stationary device, which may include a display 90 and user input buttons. Furthermore, the display 90 may be in the form of a touch screen or a similar user interface configured to accept a user input. In some examples, the reader device 46 may be utilized to track usage and status indications for a washing or sanitizing process related to the patient support apparatus 26 or a related service center. In such cases, the reader device 46 may be implemented for automatically scanning, or interrogating, the RFID tags 30, 82, 86. The controller 42 may analyze data corresponding to the RFID tags 30, 82, 86 and control the display 90 to display the data. In some examples, the controller 42 is in communication with a remote device 94 via a network 98, such as the internet, a hospital wireless infrastructure, such as an electronic medical record (EMR), an Ethernet, and the like. The controller 42 may communicate with the network 98 via a wireless communication protocol (e.g. a wide area network (WAN), Wi-Fi, Bluetooth, Bluetooth Low Energy, Zigbee, etc.) and/or wired communication (e.g., Ethernet), or any other suitable technology for exchanging data. In this way, the reader device 46 may be configured to report, or export, data to the remote device 94. In this configuration, the controller 42 may be configured to store and update the status of specific components having the RFID tags 30, 82, 86 via the network 98. The remote device 94 may be in the form of a personal computer, a mobile computing device, etc.

The RFID tags 30, 82, 86 may include the first memory unit 34 and the second memory unit 38. However, in some examples, the RFID tags 30, 82, 86 may include any number of memory units, which may include only a single memory unit 38 or three or more memory units. For example, the RFID tags 30, 82, 86 may also include a tag identifier memory 36 having approximately 160 bits of memory. The first memory unit 34 may be in the form of an identification memory unit comprising fixed identity data corresponding to the identity of the component of the patient support apparatus 26. In examples where the patient support apparatus tracking system 10 includes first and second RFID tags (i.e. 30, 82), the patient support apparatus tracking system 10 includes corresponding first and second identification memory units 34. In some aspects, first memory unit 34 is in the form of an Electronic Product Code (EPC) memory unit or bank, which may include identifying data such as the sort-prefix, a serial number, or product ID, and a date of manufacture. The serial number may include the date of manufacture. The identifying data may be read by the controller 42 to identify the component of the patient support apparatus 26 that the RFID tag 30, 82, 86 is coupled with. The sort-prefix may include two digits. In some examples, the first memory unit 34 is read-only such that the identifying data stored in the first memory unit 34 cannot be modified by the controller 42, but it is not necessarily limited to such a configuration.

Additionally, the first memory unit 34 may include a first amount of digital storage, which may be at least 96 bits of memory. The sort-prefix may be read by the reader device 46 and analyzed by the controller 42 to cingulate the RFID tag 30, 82, 86 for identifying the RFID tag 30, 82, 86. In this way, the sort-prefix may distinguish specific RFID tags (e.g., RFID tags 30, 82, 86) from various RFID tags that may be in use with the patient support apparatus tracking system 10 or related tracking systems implemented in the same location or facility. Accordingly, the component of the patient support apparatus 26 having the RFID tag 30, 82, 86 can be identified for inventory purposes.

In some examples, the sort-prefix may indicate that the RFID tag(s) 30, 82, 86 correspond to components manufactured by a specific company. The serial number or product ID may be provided such that the reader device 46 may be configured to locate and identify specific equipment within a facility. The date of manufacture may be used to determine an end of product life, a warranty timing, and/or an expiration date for the at least one of the frame 14, mattress 18, and mattress cover 22. In this way, the patient support apparatus tracking system 10 may identify and track products/components of the patient support apparatus 26 which may require scheduled maintenance, replacement, renewal, and/or updating. In some examples, the date of manufacture may be programmed in a hexadecimal numeric system such that the controller 42 may be able to read the date of manufacture without conversion. Further, data stored in the first memory unit 34 may be displayed on the display 90 and/or exported to the remote device 94. As such, the remote device 94 may provide access to the identification or location of specific components having the RFID tags 30, 82, 86 by a user. A location of a component may indicate that the component is in storage or in use.

The second memory unit 38 may be in the form of a user or programmable memory bank, which may be configured to log, or store, data, such as equipment updates, written into the RFID tag 30, 82, 86. Accordingly, the second memory unit 38 may be in the form of a read/write memory unit to facilitate the programmable operation. In this configuration, a user may provide input to the controller 42 that prompts the controller 42 to write data into the second memory unit 38. As such, the second memory unit 38 may be in the form of a service memory unit comprising configurable data corresponding to services performed on the component of the patient support apparatus 26. In examples where the patient support apparatus tracking system 10 includes first and second RFID tags (i.e. 30, 82), the patient support apparatus tracking system 10 includes corresponding first and second service memory units 38. The second memory unit 38 may include a second amount of digital storage, which may be greater than the first amount of digital storage in first memory unit 34. In some examples, the second memory unit 38 includes more than 500 bits, or up to 8K bytes of memory or more. An equipment update, or status, may include a log of types of services performed and corresponding dates/times, wash cycle dates/times, maintenance dates/times, counters and the like. For example, a counter may include a total number of times a component of the patient support apparatus 26 having the RFID tag 30, 82, 86 has been in a service center. In another example, a counter may include a total number of times a wash cycle has been performed on the component of the patient support apparatus 26 having the RFID tag 30, 82, 86.

A user may prompt the reader device 46 to write equipment updates to the RFID tag(s) 30, 82, 86. Alternatively, the reader device 46 may automatically write the equipment updates to the RFID tag(s) 30, 82, 86. As such, the reader device 46 may be configured to locate or identify equipment or components of the patient support apparatus 26, (e.g. the frame 14, mattress 18, and mattress cover 22) which may require scheduled maintenance, wash cycles, and/or services. Data included in the second memory unit 38 may be displayed on the display 90 and/or exported to the remote device 94. Thus, the remote device 94 may provide access to the identification or location of specific components having the RFID tags 30, 82, 86 identifying the status of maintenance, wash cycles, renewal, and/or specific equipment updates performed or required. In some examples, data included in the first memory unit 34 and/or the second memory unit 38 of multiple RFID tags 30, 82, 86 may be displayed on the display 90 and/or exported to the remote device 94.

Figure 3:
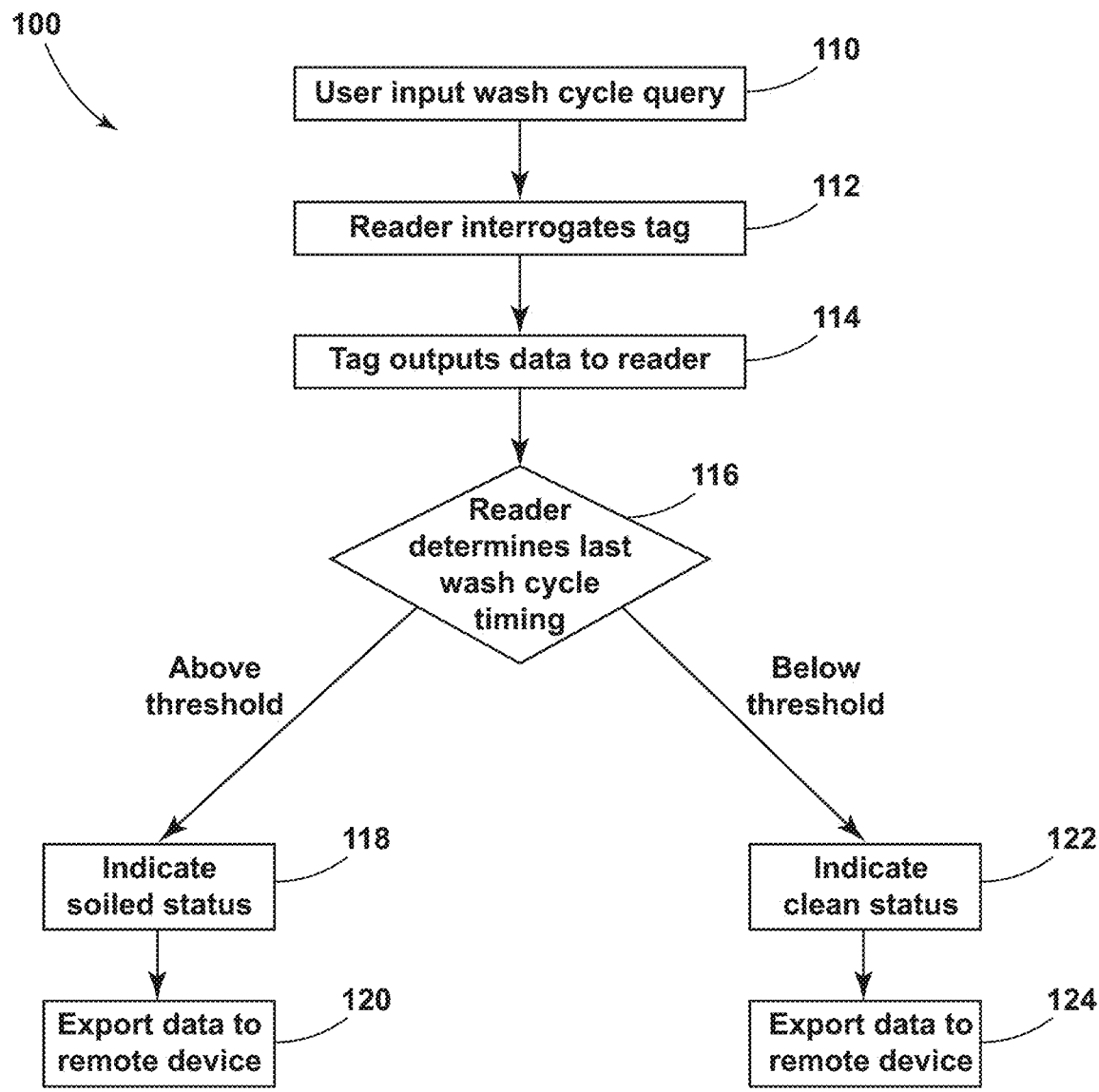
FIG. 3 is a flow chart illustrating a method of tracking a patient support apparatus equipment wash status according to various aspects described herein.

FIG. 3 illustrates a method 100 of tracking a patient support apparatus 26 equipment update, such as a wash status. The method 100 may start at step 110 where a user may input a selection to the reader device 46 that commands the reader device 46 to query RFID tags for wash cycle information. Wash cycle information may include dates/times and types of cycles, but is not limited to such examples. Next, at step 112, the reader device 46 may transmit an encoded radio signal to interrogate the RFID tag(s) 30, 82, 86. At step 114, The RFID tag(s) 30, 82, 86 receive(s) the message and may respond with information including its sort-prefix and/or serial number, which may be stored in the first memory unit 34 and communicated to the controller 42. Additionally, the RFID tag(s) 30, 82, 86 may respond with information including a log of one or more recent wash cycles, which may be stored in the second memory unit 38 and communicated to the controller 42. In some examples, the reader device 46 may discriminate among several RFID tags that may be within the range of the reader device 46 and read them simultaneously.

At step 116, the controller 42 of the reader device 46 determines if the last wash cycle timing for a specific tag, such as the RFID tag 82 embedded into the mattress cover 22 is above or below a threshold value. The threshold value may correspond to a unit of time such as a week, a month, 90 days, etc. The controller 42 may determine if the last wash cycle timing is above or below the threshold value using current date information in comparison to last wash cycle timing information. If the last wash cycle timing is above the threshold value, the controller 42 may determine that a status of the component of the patient support apparatus 26 corresponding to the RFID tag(s) 30, 82, 86 is in need of renewal or maintenance (e.g., soiled) and may control the display 90 to indicate a soiled or service required status at step 118. In some aspects, the threshold value is determined based on the identity of the component of the patient support apparatus 26 having the specific tag. Then, at step 120, the soiled status and/or the log of wash cycle timings may be exported by the controller 42 to the remote device 94. If the last wash cycle timing is below the threshold value, the controller 42 may determine that a status of the component of the patient support apparatus 26 identified by the RFID tag(s) 30, 82, 86 is clean and may control the display 90 to indicate a clean status at step 122. At step 124, the clean status and/or the log of wash cycle timings may be exported by the controller 42 to the remote device 94.

Figure 4:
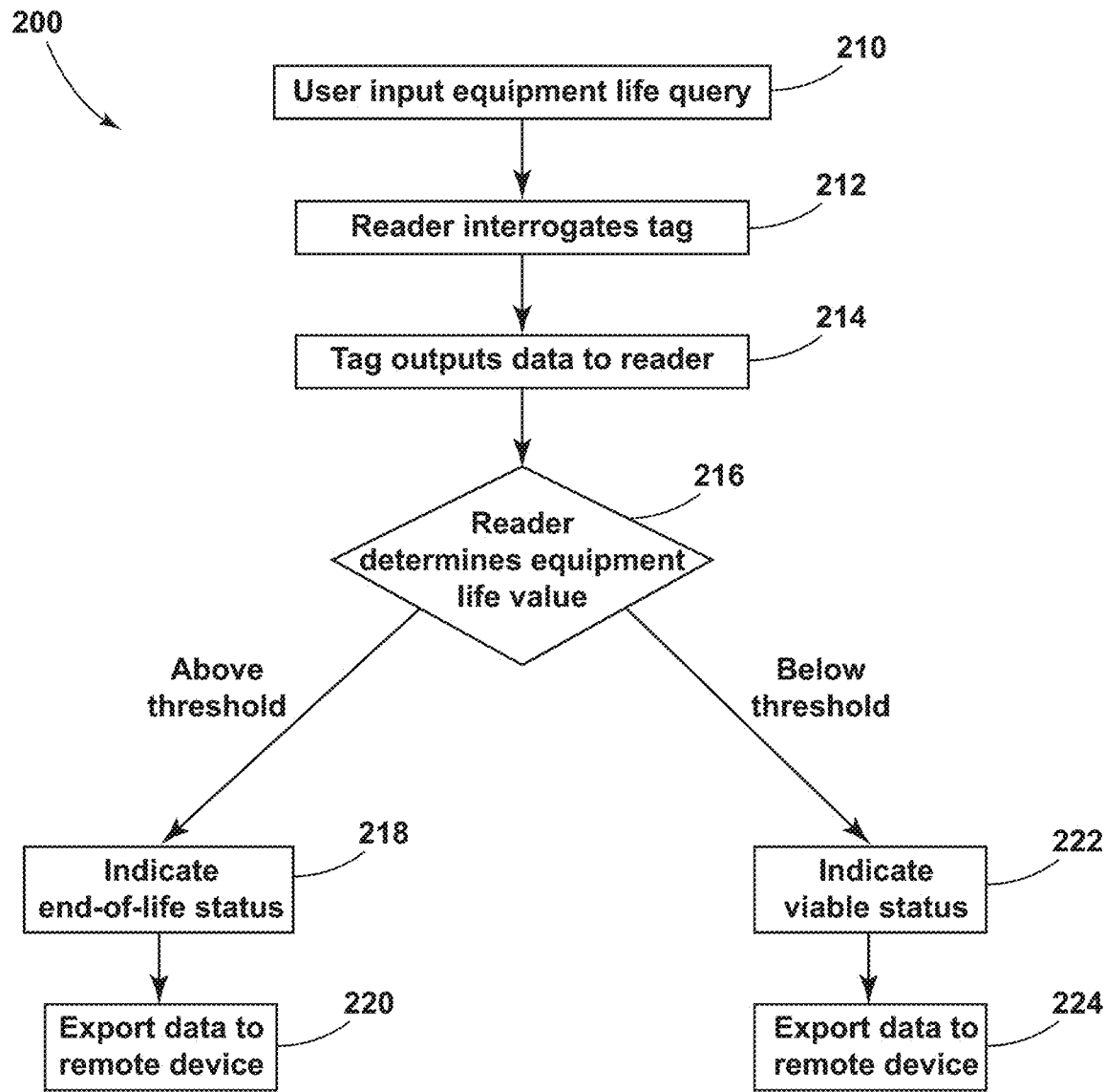
FIG. 4 is a flow chart illustrating a method of tracking a patient support apparatus equipment life status according to various aspects described herein.

FIG. 4 illustrates a method 200 of tracking a patient support apparatus 26 equipment update, such as a life status. The method 200 may start at step 210 where a user may input a selection to the reader device 46 that commands the reader device 46 to query RFID tags for equipment life information. Next, at step 212, the reader device 46 may transmit an encoded radio signal to interrogate the RFID tag(s) 30, 82, 86. At step 214, The RFID tag(s) 30, 82, 86 receive(s) the message and may respond with information including its sort-prefix and/or serial number and its date of manufacture, which may be accessed from the first memory unit 34 and communicated to the controller 42. In some examples, the reader device 46 may discriminate among several RFID tags that may be within the range of the reader device 46 and read them simultaneously. At step 216, controller 42 of the reader device 46 determines if the equipment life value for a specific tag, such as the RFID tag 30 embedded into the mattress 18 is above or below a threshold value. The threshold value may correspond to a unit of time such as a 90 days, 1 year, or 3 years, etc. In some aspects, the threshold value is determined based on the identity of the component of the patient support apparatus 26 having the specific tag. For example, the bottom cover 24 may have a higher threshold value than the top cover 23. Furthermore, the mattress 18 may have a higher threshold value than both the top cover 23 and the bottom cover 24.

The controller 42 may determine if the equipment life value is above or below the threshold value using current date information in comparison to the date of manufacture. If the equipment life value is above the threshold value, the controller 42 may determine an end-of-life status, or identity, of the component of the patient support apparatus 26 corresponding to the RFID tag(s) 30, 82, 86 and may control the display 90 to indicate an end-of-life status at step 218. Then, at step 220, the end-of-life status and/or the date of manufacture may be exported by the controller 42 to the remote device 94. If the equipment life value is below the threshold value, controller 42 may determine a viable status of the component of the patient support apparatus 26 corresponding to the RFID tag(s) 30, 82, 86 and may control the display 90 to indicate a viable status at step 222. At step 224, the viable status and/or the date of manufacture may be exported by the controller 42 to the remote device 94.

While the methods 100 and 200 have been described including steps 110-124, and 210-224, respectively, it is within the scope of the disclosure to include additional or fewer steps for tracking the patient support apparatus 26 equipment or related components. For example, steps 110 and 210 in which the user inputs a selection to the reader device 46 may not be included. Furthermore, output from multiple RFID tags 30, 82, 86 may be simultaneously displayed on the reader device at steps 122 and 218 or exported in combination to the remote device 94 at steps 120, 124, 220 and 224.

According to one aspect of the present disclosure, a patient support apparatus tracking system may include at least one of a frame, a mattress, and a mattress cover. A radio-frequency identification (RFID) tag may be embedded within the at least one of the frame, mattress, and mattress cover. The RFID tag may have a first memory unit comprising a sort-prefix and a second memory unit. The RFID tag may be configured to receive an equipment update into the second memory unit and to cingulate the RFID tag by communicating the sort-prefix from the first memory unit to a controller via a reader device.

According to another aspect of the present disclosure, the equipment update is an indication of a wash cycle timing.

According to still another aspect of the present disclosure the equipment update is an indication of a maintenance service timing.

According to yet another aspect of the present disclosure, the first memory unit is an electronic product code (EPC) memory unit.

According to still another aspect of the present disclosure, the controller is in communication with a remote device and is configured to export data from the second memory unit to the remote device.

According to still another aspect of the present disclosure, the controller is configured to read multiple RFID tags and to export data corresponding to the multiple RFID tags to the remote device.

According to yet another aspect of the present disclosure, the controller is configured to display data from the second memory unit on a reader device display to indicate equipment updates for the RFID tag.

According to another aspect of the present disclosure, the controller is configured to read multiple RFID tags and to display data corresponding to the multiple RFID tags on the reader device display to indicate equipment updates for the multiple RFID tags.

According to still another aspect of the present disclosure, the controller is configured to identify an expiration status for the least one of the frame, the mattress, and the mattress cover.

According to yet another aspect of the present disclosure, the least one of the frame, the mattress, and the mattress cover is a mattress cover.

The various illustrative logical blocks, modules, controllers, and circuits described in connection with the embodiments disclosed herein may be implemented or performed with application specific integrated circuits (ASICs), field programmable gate arrays (FPGAs), general purpose processors, digital signal processors (DSPs) or other logic devices, discrete gates or transistor logic, discrete hardware components, or any combination thereof designed to perform the functions described herein. A general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A patient support apparatus tracking system comprising:
    a first mattress cover comprising:
        a first radio-frequency identification (RFID) tag, the first RFID tag including:
            a first identification memory unit comprising first identity data for the first mattress cover, wherein the first identity data includes a sort-prefix and a serial number, wherein the first identification memory unit is read-only such that the first identity data cannot be modified; and
            a first service memory unit comprising first service data corresponding to services performed on the first mattress cover, wherein the first service memory unit is in the form of a read/write memory unit;
    a second mattress cover comprising:
        a second RFID tag, the second RFID tag including:
            a second identification memory unit comprising second identity data for the second mattress cover, wherein the second identity data includes a sort-prefix and a serial number different from the first identity data in the first RFID tag, wherein the second identification memory unit is read-only such that the second identity data cannot be modified; and
            a second service memory unit comprising second service data corresponding to services performed on the second mattress cover, wherein the second service memory unit is in the form of a read/write memory unit; and
    a controller configured to:
        singulate each of the first and second RFID tags using the sort-prefix from the first and second identification memory units;
        write an equipment update into the first and second service memory units; and
        communicate an equipment status of each of the first and second mattress covers based on the first and second identity data for the first and second mattress covers to one of a display and remote device, wherein the equipment status for each of the first and second mattress covers is determined by a threshold value based on the first and second identity data corresponding to the first mattress cover and the second mattress cover, respectively, and the threshold value for the first mattress cover is less than the threshold value for the second mattress cover.

2. The patient support apparatus tracking system of claim wherein the controller is further configured to:
    read a log of equipment updates in the first and second RFID tags;
    determine a last wash cycle timing for each of the first and second mattress covers;
    determine if the last wash cycle timing for each of the first and second mattress covers is above the corresponding threshold value;
    communicate the equipment status as soiled for either of the first and second mattress covers having a last wash cycle timing above the threshold value to one of the display and remote device; and
    communicate the equipment status as clean for either of the first and second mattress covers having a last wash cycle timing below the threshold value to one of the display and remote device.

3. The patient support apparatus tracking system of claim 1, wherein the controller is configured to read multiple RFID tags and export data corresponding to the multiple RFID tags to the remote device in combination.

4. The patient support apparatus tracking system of claim 1, wherein the controller is configured to read multiple RFID tags and control the display to simultaneously display data corresponding to the multiple RFID tags that indicate equipment statuses for the multiple RFID tags.

5. The patient support apparatus tracking system of claim 1, wherein the controller is further configured to:
    read the first and second identity data;
    determine an equipment life value from the first and second identity data for each of the first and second mattress covers;
    determine if the equipment life value for each of the first and second mattress covers is above an equipment life threshold value, wherein the equipment life threshold value is determined based on the first and second identity data for the first and second mattress covers; and
    communicate an equipment status as end-of-life for one of the first and second mattress covers having an equipment life value above the equipment life threshold value to one of the display and remote device.

6. A patient support apparatus tracking system comprising:
- at least one of a frame, mattress, and mattress cover; and
- a radio-frequency identification (RFID) tag embedded within the at least one of the frame, mattress, and mattress cover, the RFID tag comprising:
  - an identification memory unit including read-only sort-prefix data corresponding to the one of the frame, mattress, and mattress cover; and
  - a service memory unit comprising a read/write configuration including a greater amount of digital storage than the identification memory unit, wherein the RFID tag is configured to:
    - receive a log of configurable equipment updates into the service memory unit; and
    - communicate the sort-prefix from the identification memory unit and the log of equipment updates to a controller via a reader device.

7. The patient support apparatus tracking system of claim 6, wherein the identification memory unit is an electronic product code (EPC) memory unit.

8. The patient support apparatus tracking system of claim 6, wherein the identification memory unit further includes:
- a serial number and a date of manufacture corresponding to the at least one of the frame, mattress, and mattress cover.

9. The patient support apparatus tracking system of claim 6, wherein the equipment update is an indication of a wash cycle timing.

10. The patient support apparatus tracking system of claim 9, wherein the at least one of the frame, the mattress, and the mattress cover is a mattress cover.

11. The patient support apparatus tracking system of claim 10, wherein an equipment status for the mattress cover is determined using a threshold value based on the read-only sort-prefix data corresponding to the mattress cover.

12. The patient support apparatus tracking system of claim 6, wherein the controller is configured to read multiple RFID tags and to export data corresponding to the multiple RFID tags to a remote device in combination.

13. The patient support apparatus tracking system of claim 6, wherein the controller is configured to read multiple RFID tags and to control a reader device display to simultaneously display data corresponding to the multiple RFID tags that indicate equipment updates for the multiple RFID tags.

14. A patient support apparatus tracking system comprising:
- a first mattress cover comprising a first radio-frequency identification (RFID) tag, the first RFID tag including a first identification memory unit comprising first fixed data corresponding to an identity of the first mattress cover and a first service memory unit comprising first configurable data corresponding to services performed on the first mattress cover;
- a second mattress cover comprising a second RFID tag, the second RFID tag including a second identification memory unit comprising second fixed data corresponding to an identity of the second mattress cover, the second fixed data in the second RFID tag being different from the first fixed data in the first RFID tag, and a second service memory unit comprising second configurable data corresponding to services performed on the second mattress cover; and
- wherein the first and second RFID tags are configured to communicate the first and second fixed data and the first and second configurable data via a controller configured to:
  - read the first and second configurable data stored in the first and second RFID tags;
  - determine a last wash cycle timing for each of the first and second mattress covers;
  - determine if the last wash cycle timing for each of the first and second mattress covers is above a threshold value; and
  - communicate an equipment status as soiled for either of the first and second mattress covers having a last wash cycle timing above the threshold value to one of a display and remote device, wherein the threshold values are determined based on the identity of the corresponding first and second mattress covers and the threshold value for the first mattress cover is less than the threshold value for the second mattress cover.

15. The patient support apparatus tracking system of claim 14, wherein the first and second identification memory units comprise a first amount of digital storage and the first and second service memory units comprise a second amount of digital storage, greater than the first amount of digital storage, wherein the first and second service memory units are configured to store a log of equipment updates.

16. The patient support apparatus tracking system of claim 14, wherein the first and second fixed data includes a sort-prefix, a serial number, and a date of manufacture identifying the first and second mattress covers.

17. The patient support apparatus tracking system of claim 14, wherein the first and second configurable data written to the service memory units include an indication of a wash cycle timing.

18. The patient support apparatus tracking system of claim 14, wherein the first mattress cover comprises a breathable material and the second mattress cover comprises a waterproof material.

* * * * *